(12) United States Patent
Mattke et al.

(10) Patent No.: US 8,816,126 B2
(45) Date of Patent: Aug. 26, 2014

(54) PROCESS FOR PREPARING ISOCYANATES

(75) Inventors: Torsten Mattke, Freinsheim (DE); Gerhard Olbert, Dossenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/587,378

(22) Filed: Aug. 16, 2012

(65) Prior Publication Data

US 2013/0060062 A1    Mar. 7, 2013

Related U.S. Application Data

(60) Provisional application No. 61/530,433, filed on Sep. 2, 2011.

(51) Int. Cl.
   *C07C 263/00* (2006.01)
   *C07C 263/10* (2006.01)

(52) U.S. Cl.
   CPC .................................. *C07C 263/10* (2013.01)
   USPC ........................................................ 560/347

(58) Field of Classification Search
   None
   See application file for complete search history.

(56) References Cited

U.S. PATENT DOCUMENTS

| | | | |
|---|---|---|---|
| 4,128,569 A * | 12/1978 | Horn et al. ..................... | 560/347 |
| 2003/0114705 A1 | 6/2003 | Friedrich et al. | |
| 2009/0221846 A1 | 9/2009 | Wölfert et al. | |
| 2011/0213177 A1 | 9/2011 | Mattke et al. | |
| 2011/0230676 A1 | 9/2011 | Lehr et al. | |
| 2011/0251425 A1 | 10/2011 | Penzel et al. | |
| 2012/0095255 A1 | 4/2012 | Mattke et al. | |
| 2012/0172621 A1 | 7/2012 | Mattke et al. | |
| 2012/0226073 A1 | 9/2012 | Heinen et al. | |
| 2012/0251435 A1 | 10/2012 | Lehr et al. | |
| 2012/0253063 A1 | 10/2012 | Mattke et al. | |

FOREIGN PATENT DOCUMENTS

| | | |
|---|---|---|
| EP | 1 319 655 A2 | 6/2003 |
| WO | WO 2007/028715 A1 | 3/2007 |
| WO | WO 2010/015667 A1 | 2/2010 |
| WO | WO 2011/003531 A1 | 1/2011 |
| WO | WO 2011/036062 A2 | 3/2011 |
| WO | WO 2011/067369 A1 | 6/2011 |
| WO | WO 2011/104264 A1 | 9/2011 |
| WO | WO 2011/113737 A1 | 9/2011 |
| WO | WO 2012/049158 A1 | 4/2012 |
| WO | WO 2012/117003 A1 | 9/2012 |
| WO | WO 2012/130788 A1 | 10/2012 |
| WO | WO 2012/163894 A2 | 12/2012 |

OTHER PUBLICATIONS

"Isocyanates, Organic" in Ullmann's Encyclopedia of Industrial Chemistry, Six et al., Published Online: Jan. 15, 2003, DOI: 10.1002/14356007.a14_611, Wiley-VCH Verlag GmbH & Co. KGaA , pp. 63-82.*
U.S. Appl. No. 13/687,670, filed Nov. 28, 2012, Mattke, et al.
U.S. Appl. No. 13/661,652, filed Oct. 26, 2012, Leschinski, et al.
U.S. Appl. No. 14/058,765, filed Oct. 21, 2013, Mattke, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

Process for preparing isocyanates by reacting the corresponding amines comprised in at least one feed stream A with phosgene comprised in at least one feed stream P in a reaction plant comprising at least one mixing zone and at least one reaction zone, wherein feed stream A and/or feed stream P optionally comprise one or more inert materials and,
during periods of time in which the flow $S^x$ of the amine used is below the flow $S^0$ of the amines used during operation at the nominal capacity of the reactor plant,
(i) the ratio of phosgene to amine is increased and/or
(ii) the concentration of the inert material or materials in the amine-comprising feed stream A and/or the phosgene-comprising feed stream P is increased
compared to operation at the nominal capacity of the reactor.

14 Claims, No Drawings

PROCESS FOR PREPARING ISOCYANATES

This patent application claims the benefit of U.S. provisional patent application Ser. No. 61/530,433 filed Sep. 2, 2011, incorporated in its entirety herein by reference.

The invention relates to a process for preparing isocyanates by reacting the corresponding amines with phosgene, in which, during operation below the nominal capacity of the reactor plant used, the amount of phosgene is increased and/or the amount of inert materials added is increased.

The preparation of isocyanates by phosphenation of the corresponding amines can in principle be carried out by means of a liquid-phase phosgenation or a gas-phase phosgenation. Unlike the gas-phase phosgenation, the reaction in the liquid-phase phosgenation is carried out at low temperatures, and vaporization of the starting materials is not necessary.

In liquid-phase phosgenation, an amine-comprising feed stream in liquid form is fed in. This is mixed with a phosgene-comprising feed stream. The phosgene can here be dissolved in an inert solvent. The phosgene-comprising feed stream is subsequently injected into a mixing device in which it mixes with the amine-comprising feed stream. The amine and the phosgene react with liberation of HCl to form the corresponding isocyanate.

Rapid mixing of the amine with the phosgene is necessary since, at an insufficient phosgene concentration, the isocyanate formed reacts with the excess amine to form urea or other troublesome, high-viscosity and solid by-products. For this reason, rapid mixing and a short residence time in the reaction chamber are necessary.

A process for the liquid-phase phosgenation of amines for preparing isocyanates is described, for example, in WO 2010/015667 A1.

In gas-phase phosgenation, an amine-comprising feed stream and a phosgene-comprising feed stream, each in the gaseous state, are mixed. The amine and the phosgene react with liberation of HCl to form the corresponding isocyanate. The amine-comprising feed stream is generally present in liquid form and has to be vaporized and optionally superheated before mixing with the phosgene-comprising stream.

Owing to the low vapor pressure in particular of the diamines, the vaporization is carried out at elevated temperature. However, this can cause decomposition reactions of the amines or diamines, for example deaminations, demethylations and dimerizations, which have an adverse effect on the selectivity of the overall process.

In addition, reactions quickly commence on contacting of the two feed streams as a result of the high temperatures. Apart from phosgenation of the amine to form isocyanate, it is possible for undesirable secondary and subsequent reactions to take place. Thus, for example, isocyanate which has already been formed can react with as yet unreacted amine to form a urea. Furthermore, carbodiimides and cyanurates can also be formed. This firstly affects the selectivity of the process, and, secondly, solid by-products which have been formed can lead to blockages and thus have an adverse effect on the running time of the plant. Efforts are therefore generally made to mix the feed streams as quickly as possible in order to avoid, as far as possible, mixing ratios which accelerate the formation of secondary components.

A process for preparing (poly)isocyanates in the gas phase with optimized mixing of the reactants is described, for example, in EP 1 319 655 A2.

Thus, mixing of the starting materials and the residence time of the reaction mixture in the corresponding reaction spaces are critical parameters both in gas-phase phosgenation and in liquid-phase phosgenation. The plants for preparing isocyanates by phosgenation of amines therefore have to be matched to the specific requirements in respect of rapid mixing of the feed streams and a narrow residence time window.

Plants for the phosgenation of amines are designed essentially for the maximum streams of materials or for the respective nominal capacity. This means both mixing devices such as nozzles and also the reaction spaces, for example residence reactors, operate at the nominal capacity in the optimal region with optimized yield, purity of the products, etc. However, if the plant is not operating at full load, i.e. it is operated at only part of the nominal capacity, the residence times, for example, alter and the plant is no longer operating in the optimal region. This is the case, for example, during start-up and running-down, part loading of the plant or malfunctions in the plant. In these cases of reduced load, both the mixing devices and the residence reactors do not operate in the optimal region. The consequences are decreases in yield, fouling problems and/or reductions in quality.

It was therefore an object of the present invention to provide a process for preparing isocyanates by reacting the corresponding amines with phosgene, which process can also be carried out at various load states without the above-described problems; in particular, mixing and/or the reaction should occur in the respective optimized residence time window even when the plant is operated at part load.

This object is achieved according to the invention by the following process for preparing isocyanates by reacting the corresponding amines comprised in at least one feed stream A with phosgene comprised in at least one feed stream P in a reactor plant comprising at least one mixing zone and at least one reaction zone, wherein feed stream A and/or feed stream P optionally comprise one or more inert material(s) and, during periods of time in which the flow $S^x$ of the amine used is below the flow $S^0$ of the amines used during operation at the nominal capacity of the reactor plant, (i) the ratio of phosgene to amine is increased and/or
(ii) the concentration of the inert material or materials in the amine-comprising feed stream A and/or the phosgene-comprising feed stream P is increased compared to operation at the nominal capacity of the reactor.

The process of the invention allows an existing plant to be operated at different loads with constant product and process quality. This may save the acquisition of a plurality of plants having different nominal capacities.

The nominal capacity is the amount of the target product of a chemical plant which is produced per unit time and for which the plant was designed and dimensioned. Operation at the nominal capacity therefore also implies the flows (amounts per unit time) used for achieving the nominal capacity of a plant. In the preparation of isocyanates from the corresponding amines and phosgene, this means that a reactor plant is designed for production of a particular amount of isocyanate in a particular period of time and particular flows of amine and phosgene have to be introduced for this purpose.

For the purposes of the invention, the term "below nominal capacity" refers to the amine or amines used; i.e. "operation below nominal capacity" means that the flow of amine introduced is less than the flow of amine provided for operation at nominal capacity of a reactor plant. Parameters which relate to operation at nominal capacity are in the present text denoted by the index "0". Parameters which relate to operation below the nominal capacity are indicated by "x".

According to the invention, the flow $S^0$ of the amines means the amount of amine fed per unit time to the reactor plant when the reactor plant is operated at its nominal capacity. Furthermore, the flow $S^x$ of the amines means the amount of amine fed per unit time to the reactor plant when the reactor is operated below its nominal capacity.

The total flow $G^0$ means the sum of the flows introduced during operation at the nominal capacity of the plant, calculated as the sum of the flows of amine(s), phosgene and any inert materials present. The total flow $G^x$ means the sum of the flows introduced during operation below the nominal capacity of the plant, calculated as the sum of the flows of amine(s), phosgene and any inert materials present.

In a preferred embodiment, the flow $S^x$ of the amines is below 95% of the flow $S^0$ of the amines, more preferably below 90% and particularly preferably below 85% of the flow $S^0$ of the amines, for at least part of the time.

The present invention relates to a process for preparing isocyanates by reacting phosgene with the corresponding amines, in which a given reactor plant is usually operated for at least part of the time below its nominal capacity.

"Part of the time" in the present context usually comprises periods of time of at least 6 hours, preferably at least 12 hours and particularly preferably at least 24 hours. The periods of time for which the reactor plant can be operated below its nominal capacity have no upper limit, so that a reactor plant can also be operated continuously according to the process of the invention below the nominal capacity, i.e. the flow of the amine or amines used is continuously below the flow of the amines used at nominal capacity of the reactor plant used. It is also possible, according to the invention, to change back and forth between operation at nominal capacity and operation below nominal capacity when employing the measures provided according to the invention.

In one variant of the process of the invention, the ratio of phosgene fed in to amine fed in is increased (i) during operation below the nominal capacity of the reactor plant employed.

In a further variant of the process of the invention, the concentration of the inert material or materials in the feed stream A and/or in the feed stream P is increased (ii). Feed stream A and/or feed stream P optionally comprise one or more inert materials which are selected from among the inert media indicated below, preferably inert solvents and inert gases. If feed stream A or P does not comprise any inert materials during operation at nominal capacity, increasing the concentration of the inert material or materials means that one or more inert materials are added to the feed stream A and/or the feed stream P, i.e. the concentration of inert materials is increased from 0 to a higher value.

For the purposes of the present invention, inert materials, also referred to as inert media, whose concentration can be increased according to variant (ii) are generally ones which are present in the reaction space and do not react with the compounds occurring during the course of the reaction. The inert material or materials are preferably selected from among inert solvents and inert gases. The inert solvents can, depending on the way in which the reaction is carried out, be present in liquid or gaseous form. As inert medium, it is possible to use, for example, nitrogen, noble gases such as helium or argon, aromatics such as chlorobenzene, o-dichlorobenzene, trichlorobenzene, toluene, xylene, chloronaphthalene, decahydronaphthalene, carbon dioxide or carbon monoxide. However, preference is given to using nitrogen and/or chlorobenzene as inert medium in reaction in the gas phase. In the case of a reaction in the liquid phase, the concentration of the solvent or solvents which is/are usually used is preferably increased in variant (ii).

The variants (i) and (ii) can also be combined with one another, for example be employed at the same time.

In an embodiment of the invention, the total flow of $G^x$ is increased by means of the above-described measures (i) and/or (ii) to such an extent that the total flow $G^x$ during operation below the nominal capacity is at least (x+5) % of the total flow $G^0$ during operation at the nominal capacity, where x % indicates the percentage of the flow of amine(s) to which the flow of amine(s) is reduced compared to operation at nominal capacity. $G^x$ is preferably at least (x+8) % of the total flow $G^0$ and is particularly preferably at least (x+12) % of the total flow $G^0$. If the reactor plant is, for example, operated using 50% of the flow of amine(s), based on the nominal capacity, $G^x$ is increased by the above-described measures (i) and/or (ii) to such an extent that the total flow $G^x$ is at least 55%, preferably at least 58% and particularly preferably at least 62%, of the total flow $G^0$.

In a further embodiment of the invention, the total flow $G^x$ is increased by the above-described measures (i) and/or (ii) to such an extent that it is in the range $(G^0-15\%) \leq G^x \leq (G^0+15\%)$, preferably in the range $(G^0-10\%) \leq G^x \leq (G^0+10\%)$, particularly preferably in the range $(G^0-5\%) \leq G^x \leq (G^0+5\%)$ and in particular essentially $G^0$.

To prepare the isocyanate, the at least one phosgene-comprising feed stream P and the at least one amine-comprising feed stream A are firstly fed to a mixing zone in which the mixing of amine-comprising feed stream A and phosgene-comprising feed stream P occurs to form a reaction mixture. Here, care has to be taken to ensure sufficiently rapid mixing of the reactants. Methods of achieving short mixing times are known in principle. In the mixing units, it is possible to use mixing apparatuses having dynamic or static mixers. According to the invention, preference is given to using one or more static mixing devices in the mixing units. Suitable static mixing devices are, for example, nozzles, flat jet nozzles or Venturi nozzles and also Laval nozzles known from combustion technology. A particularly advantageous embodiment of a static mixing device is described in WO2010/015667 A1. As dynamic mixers, it is possible to use, for example, rotor/stator systems arranged in the mixing units. Preference is given, according to the invention, to using static mixing devices, in particular nozzles.

After mixing of the feed streams to form at least one reaction mixture, the reaction mixture is reacted in a reaction zone comprising the at least one reaction unit. Reactors which can be used as reaction units for phosgenation of an amine to produce isocyanates are known to those skilled in the art. A reaction zone preferably comprises at least one residence reactor. Preference is given to using reaction columns, tube reactors and/or cascades of stirred vessels as residence reactors.

In the reaction zone, the amine is reacted with the phosgene to form the corresponding isocyanate and hydrogen chloride. The phosgene is usually added in excess, so that the reaction mixture formed in the reaction zone comprises the isocyanate formed and the hydrogen chloride and also phosgene.

According to the invention, the reaction zone comprises at least one reaction unit and the mixing zone comprises at least one mixing unit.

For the purposes of the invention, a "unit" (for example mixing unit, reaction unit or quenching unit) is in each case an apparatus in which the respective process step (for example mixing, reaction or quenching) can be carried out. As reaction unit, it is possible to use, for example, a tube reactor; as mixing unit it is possible to use a dynamic mixer having a rotor/stator system; and as quenching unit, it is possible to use an apparatus suitable for quenching.

After the reaction to form isocyanate, the work-up of the product mixture obtained in the reaction is carried out. The work-up includes, for example, isolation of the desired isocyanates, removal of any solvents, inert gases, starting materials and quenching media comprised in the product mixture, any optional scrubbing of the product mixture and condensations.

The process of the invention is suitable both for gas-phase phosgenation and for liquid-phase phosgenation.

In an embodiment of the invention, the reaction of amine and phosgene in the reaction zone occurs in the gas phase. For this purpose, the pressure in the reaction zone is usually in the range from 0.3 to 3 bar absolute, preferably in the range from 0.8 to 3.0 bar absolute. The temperature is usually in the range from 250 to 550° C., preferably in the range from 300 to 500° C.

To be able to carry out the reaction in the gas phase, the amine and the phosgene are preferably introduced in gaseous form. For this purpose, the amine preferably has a temperature in the range from 200 to 400° C. The pressure in the mixing zone is preferably in the range from 0.05 to 3 bar absolute and the temperature in the mixing zone is in the range from 200 to 400° C. The temperature in the mixing zone is determined by the temperature of the phosgene and amine flowing into the mixing zone. The temperature of the phosgene introduced is preferably in the range from 250 to 450° C. For this purpose, the phosgene is usually heated in a manner known to those skilled in the art before introduction.

Heating of the phosgene and the amine and vaporization of the amine are carried out using, for example, electric heating or direct or indirect heating by combustion of a fuel. Fuels used are usually fuel gases, for example natural gas. However, heating by means of, for example, steam is also possible when the boiling point is reduced by decreasing the pressure of the amine. The pressure of the steam is selected as a function of the boiling point of amine. A suitable steam pressure is, for example, in the range from 40 to 100 bar. This corresponds to a temperature of the steam in the range from 250 to 311° C. However, it is also possible to use steam having a temperature of greater than 311° C. for vaporizing the amine.

It is generally necessary to heat the amine in a number of stages to the reaction temperature. In general, the amine is for this purpose firstly preheated, then vaporized and subsequently superheated. In general, the vaporization requires the longest residence times and thus leads to decomposition of the amine. To minimize this, vaporization at relatively low temperatures, as results, for example, from the lower pressure, is advantageous. To superheat the vaporized amine to the reaction temperature after vaporization, heating by means of steam is generally not sufficient. Superheating is therefore usually carried out using electric heating or direct or indirect heating by combustion of a fuel.

In contrast to the vaporization of the amine, the vaporization of the phosgene is generally carried out at significantly lower temperatures. For this reason, steam can generally be used for vaporizing the phosgene. However, the superheating of the phosgene which is required to heat this to the reaction temperature is generally also possible only by means of electric heating or direct or indirect heating by combustion of a fuel.

Preferably, the at least one amine-comprising feed stream A and the at least one phosgene-comprising feed stream P are in each case converted into the gaseous phase in at least one vaporization zone and optionally superheated further in at least one superheating zone.

A vaporization zone comprises at least one vaporization unit, a superheating zone comprises at least one superheating unit.

The same applies to the at least one phosphene-comprising feed stream P. Preference is given to both the at least one amine-comprising feed stream A and the at least one phosgene-comprising feed stream P being in each case converted into the gaseous phase in at least one vaporization zone and superheated in at least one superheating zone.

The reaction in the gas phase can be carried out in the presence of at least one inert medium. The inert medium can be added to the phosgene-comprising feed stream and/or to the amine-comprising feed stream.

In general, the inert medium is used in such an amount that the ratio of the gas volumes of inert medium to amine and to phosgene is from <0.0001 to 30, preferably from <0.01 to 15 and particularly preferably from <0.1 to 5.

To avoid formation of by-products, phosgene is preferably introduced in excess. In order to introduce only the proportion of amines necessary for the reaction, it is possible to mix the amine with an inert gas. The amount of amine fed in at a prescribed geometry of the inlet openings for the amine and the phosgene can be adjusted via the proportion of inert gas in the amine.

It is desirable in the gas-phase phosgenation that the compounds occurring during the course of the reaction, i.e. starting materials (amine and phosgene), intermediates (in particular the monocarbamoyl and dicarbamoyl chlorides formed as intermediates), end products (diisocyanate) and also any inert compounds fed in, remain in the gas phase under the reaction conditions. Should these or other components separate out from the gas phase, for example on the reactor wall or other components of the apparatus, the heat transfer or the flow through the components concerned can be undesirably altered by these deposits. This applies particularly in the event of deposition of the amine hydrochlorides which are formed from free amino groups and hydrogen chloride, since the resulting amine hydrochlorides precipitate easily and are difficult to vaporize again.

To reduce or avoid the formation of undesirable by-products and also supress decomposition of the isocyanate formed, the reaction gas is preferably cooled in a quench immediately after the reaction. For this purpose, a preferably liquid quenching medium is introduced. Vaporization of the quenching medium takes up heat and leads to rapid cooling of the reaction gases.

In a preferred embodiment of the process, the product mixture obtained in the gas-phase phosgenation is cooled in at least one quenching zone. Quenching is carried out in a quenching zone made up of at least one quenching unit.

Rapid cooling is achieved, in particular, by the quenching medium being introduced in finely atomized form. As a result, the quenching medium has a large surface area and can quickly take up heat and thus cool the reaction gas.

Particularly when a quenching medium which under the conditions in the quenching space has a boiling point below the condensation temperature of the reaction gas is used, the pressure in the feed lines is higher than the pressure in the quenching space in order to avoid vaporization of the quenching medium before introduction into the quenching space.

The pressure at which the quenching medium is introduced is preferably in the range from 1 to 20 bar, more preferably in the range from 1 to 10 bar and in particular in the range from 1 to 8 bar.

The quenching medium used for cooling preferably comprises a solvent selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene and toluene.

The quenching medium preferably comprises part of the product stream cooled in the quench; particular preference is given to using part of the product stream which has already been cooled in the quench as quenching medium. In this case, the quenching medium usually does not comprise any solvent but only the part of the product stream condensed out during quenching.

To avoid formation of deposits in pipes, regulating devices and other parts of the apparatus, in particular in the atomizer nozzles of the quench, any solid particles comprised in the quenching medium are removed before introduction into the quench.

When an isocyanate is present in the quenching medium, particular preference is given to the isocyanate formed in the reaction firstly being cooled in the quench and optionally in subsequent cooling stages and, after cooling, a substream being used as quenching medium.

The quenching medium is preferably introduced in liquid form to achieve rapid cooling of the reaction gas in the quench. The temperature of the quenching medium is preferably in the range from 0 to 250° C., in particular in the range from 20 to 220° C. Introduction of the quenching medium into the hot reaction gas results in the quenching medium being heated and/or vaporized. The heat necessary for heating and vaporization of the quenching medium is taken from the reaction gas and the reaction gas is cooled in this way. The temperature to which the reaction gas is cooled can be set, for example, via the amount and the temperature of the quenching medium introduced.

To adjust, if necessary, the temperature of the quenching medium when introduced into the quench, the quenching medium is preferably passed through a heat exchanger. Depending on the temperature of the quenching medium on entry into the heat exchanger, the quenching medium can be heated or cooled in the heat exchanger. Cooling is necessary when, for example, part of the product stream which is used as quenching medium is taken off immediately after the quench. Heating can be required when, for example, part of the product stream which is used as quenching medium is taken off at the end of the treatment section and has a temperature which is lower than the desired temperature at which the quenching medium is to be introduced into the quench. However, it will generally be necessary to cool the quenching medium before introduction into the quench.

When the quenching medium comprises solvent, the solvent/solvents is/are preferably added to the quenching medium before introduction into the quench. Solvent losses in the quenching medium can be compensated in this way. Suitable solvents which can be comprised in the quenching medium are, for example, optionally halogen-substituted hydrocarbons. The solvent comprised in the quenching medium is preferably selected from the group consisting of monochlorobenzene, dichlorobenzene, trichlorobenzene, hexane, benzene, 1,3,5-trimethylbenzene, nitrobenzene, anisole, chiorotoluene, o-dichlorobenzene, diethyl isophthalate, dimethyl isophthalate, tetrahydroforan, dimethylformamide, xylene, chloronaphthalene, decahydronaphthalene and toluene.

In a preferred embodiment the quench is followed, to effect further treatment, by further stages for cooling the reaction gas. In each of the individual cooling stages, further cooling of the product stream occurs until the desired temperature at which the product stream is fed to, for example, a subsequent work-up has been reached. Preference is given to the entire stream leaving the quench, which comprises both the quenching medium and the reaction mixture, being used as product stream in the quench.

The further cooling stages which can follow the quench can, for example, be further quenches or condensors or in any other cooling stages known to those skilled in the art. Preference is given to at least one of the stages for cooling the product stream which follow the quench being a condensor. Suitable condensors are any condensors having a construction known to those skilled in the art. A heat exchanger through which a cooling medium flows is usually used as condensor. As coolant, it is possible, for example, to use water. In this case, the gas condenses at least partly on the walls of the condensor. The liquid formed in this way runs down and is collected and taken off from the condensor.

The condensation of the product stream is generally followed by a work-up. It is thus possible, for example, to scrub the condensed mixture in a solvent. As solvent, it is possible to use, for example, the same materials which can also be used as quenching medium.

It is also possible, for example, to scrub the reaction gas leaving the quench and any cooling stages following this by means of a solvent, preferably at temperatures of greater than 130° C. Suitable solvents are, for example, the same materials which can also be used as quenching medium.

As an alternative to cooling the product stream, it is also possible to feed the product stream leaving the quench to a separation stage. However, such a separation stage can, as an alternative, also follow, for example, the condensor. However, the separation stage preferably directly follows the quench. Suitable separation stages are, for example, distillation columns or scrubbers.

When the separation stage is a scrubber, the product stream leaving the quench is preferably scrubbed by means of a solvent. Here, the isocyanate is selectively transferred into the scrubbing solution. The remaining gas and the scrubbing solution obtained are then preferably separated by means of rectification into isocyanate, solvent, phosgene and hydrogen chloride. A suitable scrubber is, in particular, a scrubbing tower in which the isocyanate formed is separated from the gaseous product stream by condensation in an inert solvent, while excess phosgene, hydrogen chloride and optionally the inert medium pass through the scrubbing tower in gaseous form. The temperature of the inert solvent is preferably kept above the dissolution temperature of the carbamoyl chloride corresponding to the amine in the scrubbing medium selected. The temperature of the inert solvent is preferably kept above the melting point of the carbamoyl chloride corresponding to the amine.

Suitable scrubbers are any scrubbers known to those skilled in the art. Thus, for example, it is possible to use stirred vessels or other conventional apparatuses, for example columns or mixer-settler apparatuses.

The scrubbing and the work-up of the mixture of reaction gas and quenching medium leaving the quench is generally carried out as described, for example, in WO-A 2007/028715.

When the separation stage is a distillation column, also referred to as rectification column, the gaseous product stream is fed into the rectification column. The rectification column is preferably operated in such a way that the temperature at the top of the rectification column is lower than the boiling point of the product stream. As a result, individual constituents of the product stream are condensed out selectively in the distillation column and can be taken off from the column at the bottom, overhead and optionally via side offtakes.

When a condensor is used for working up the product stream, the quenching medium is preferably taken off from the condensor. In the case of a work-up by rectification, the solvent used as quenching medium is preferably separated off. In this case, the solvent still comprises proportions of isocyanates. The mixture of solvent and isocyanate which has been separated off in this way is then used as quenching medium.

When part of the product stream is used as quenching medium, it is possible, for example, to branch off this part from the product stream after cooling. As an alternative, the quenching medium can also be branched off from any stream after a work-up following the quench.

In a further embodiment of the invention, the reaction is carried out in the liquid phase. This embodiment will be described in detail below. According to the invention, the amine is preferably present as solution or as suspension of the corresponding hydrochloride in the at least one amine-comprising feed stream.

As feed streams for the process of the invention with liquid-phase phosgenation, use is usually made of, firstly, from 3% strength by weight to 100% strength by weight, preferably from 50% strength by weight to 100% strength by weight, phosgene solutions and, secondly, from 5% strength by weight to 95% strength by weight solutions or suspensions of amines or salts thereof in suitable solvents.

Suitable solutions for producing the phosgene solutions and amine solutions or suspensions are any solvents which are inert under the reaction conditions, for example monochlorobenzene, o-dichlorobenzene, trichlorobenzene, toluene, xylene, methylene chloride, perchloroethylene, trichlorofluoromethane, butyl acetate, hexane, heptane, octane, biphenyl, ethyl acetate, 1,2-diacetoxyethane, 2-butanone, acetonitrile and sulfane. Any mixtures of the solvents mentioned by way of example can of course also be used. It is advantageous to use the same solvent or solvent mixture for the amine component and the phosgene, although this is not absolutely necessary for the purposes of the invention.

In a preferred embodiment of the invention, the introduction of the starting materials is set and/or regulated so that the phosgene solutions and amine solutions or amine suspensions are introduced into the mixing chamber in such amounts that a molar ratio of phosgene to primary amino groups of from about 15:1 to 1:1, preferably from 10:1 to 2:1, prevails in the mixing chamber.

In a preferred embodiment, the solution of phosgene, i.e. the phosgene-comprising feed stream P, is free of isocyanates. This means that isocyanates are present in an amount of less than or equal to 5% by weight, preferably less than 2% by weight, in particular less than 1% by weight, in the phosgene-comprising feed stream P. Particular preference is given to no isocyanates being comprised in the phosgene-comprising feed stream P, i.e. these cannot be detected by conventional analytical methods. This can advantageously significantly reduce the formation of reaction by-products such as urea derivatives which have an adverse effect on the selectivity of the process and can lead to fouling of the plant through to blockages. The formation of urea derivatives is thus reduced by no isocyanates which can lead to formation of urea derivatives on contact with amines being introduced as starting materials into the process.

When carrying out the process with liquid-phase phosgenation, the temperature in the mixing zone is usually kept at a temperature above the decomposition temperature of the carbamoyl chloride corresponding to the amine used. In the case of most amines, the process of the invention is carried out at a temperature of from about 30° C. to 300° C., preferably from about 40° C. to 150° C., particularly preferably from about 50° C. to 120° C.

The phosgenation in the liquid phase according to the invention gives at least one product mixture which is usually fed directly to the work-up and is there partially separated into HCl, phosgene, solvents and also products and by-products formed.

In general, the amines known to those skilled in the art for the preparation of isocyanates can be used in the process of the invention. These are, for example, monoamines, diamines, triamines and higher-functional amines. Preference is given to using monoamines and diamines, particularly preferably diamines. Depending on the amines used, the corresponding monoisocyanates, diisocyanates, triisocyanates or higher-functional isocyanates are obtained. Preference is given to preparing monoisocyanates or diisocyanates by the process of the invention.

Amines and isocyanates can be aliphatic, cycloaliphatic or aromatic. The amines are preferably aliphatic or cycloaliphatic, particularly preferably aliphatic.

Cycloaliphatic isocyanates are those which comprise at least one cycloaliphatic ring system.

Aliphatic isocyanates are those which have exclusively isocyanate groups bound to straight or branched chains.

Aromatic isocyanates are those which have at least one isocyanate group bound to at least one aromatic ring system.

In the following, the term (cyclo)aliphatic isocyanates will be used for cycloaliphatic and/or aliphatic isocyanates.

Examples of aromatic monoisocyanates and diisocyanates are preferably those having from 6 to 20 carbon atoms, for example phenyl isocyanate, monomeric 2,4'- and/or 4,4'-methylenedi(phenyl isocyanate) (MDI) and higher oligomers thereof (polymethylenedi(phenyl isocyanate) (PDMI) and mixtures thereof, tolylene 2,4- and/or 2,6-diisocyanate (TDI) and naphthyl 1,5- or 1,8-diisocyanate (NDI).

Examples of (cyclo)aliphatic diisocyanates are aliphatic diisocyanates such as tetramethylene 1,4-diisocyanate, hexamethylene 1,6-diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, 1,5-diisocyanatopentane, neopentane diisocyanate, 2-methyl-1,5-diisocyanatopentane, derivates of lysine diisocyanate, tetramethylxylylene diisocyanate (TMXDI), trimethylhexane diisocyanate or tetramethylhexane diisocyanate, and 3 (or 4), 8 (or 9)-bis(isocyanatomethyl)tricyclo[5.2.1.0$^{2.6}$]decane isomer mixtures, and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatornethyl)-cyclohexane, 2,4- or 2,6-diisocyanato-1-methylcyclohexane.

Preferred (cyclo)aliphatic diisocyanates are 1,6-diisocyanatohexane, 1-isocyanato-3,3,5-trimethyl-5-(isocyanatomethyl)cyclohexane and 4,4'-di(isocyanatocyclohexyl)-methane. Particular preference is given to 1,6-diisocyanatohexane, 1,5-diisocyanatopentane, 1-isocyanato-3,3,5-trimethyl-5-(isocyanatomethyl)cyclohexane and 4,4'-di(isocyanatocyclohexyl)methane.

Suitable amines which can be used in the process of the invention with gas-phase phosgenation for reaction to form the corresponding isocyanates are those in the case of which the amine, the corresponding intermediates and the corresponding isocyanates are present in gaseous form under the selected reaction conditions. Preference is given to amines which decompose to an extent of not more than 2 mol %, particularly preferably not more than 1 mol % and very particularly preferably not more than 0.5 mol %, under the reaction conditions during the time of the reaction. Particularly suitable amines here are amines, in particular diamines, based on aliphatic or cycloaliphatic hydrocarbons having from 2 to 18 carbon atoms. Examples are 1,6-diaminohexane, 1,5-diaminopentane, 1,3-bis(aminomethyl)cyclohexane, 1-amino-3,3,5-trimethyl-5-aminomethylcyclohexane (IPDA) and 4,4-diaminodicyclohexyl-methane. Preference is given to using 1,6-diaminohexane (HDA).

The process of the invention with gas-phase phosgenation can likewise be carried out using aromatic amines which can be converted without significant decomposition into the gas phase. Examples of preferred aromatic amines are toluenediamine (TDA), as 2,4 or 2,6 isomer or as a mixture thereof, for example as a from 80:20 to 65:35 (mol/mol) mixture, diaminobenzene, 2,6-xylidine, naphthyldiamine (NDA) and 2,4'-, 2,2'- or 4,4'-methylenedi(phenylamine) (MDA) or isomer mixtures thereof. Among these, preference is given to the diamines, particularly preferably 2,4- and/or 2,6-TDA and also 2,4'- and/or 4,4'-MDA.

In the gas-phase phosgenation according to the process of the invention, the amine is particularly preferably selected from the group consisting of 1,6-diaminohexane, monomeric 2,4'-methylenedi(phenylamine), monomeric 4,4'-methylenedi(phenylamine), 2,4-toluenediamine, 2,6-toluenediamine, 1-amino-3,3,5-trimethyl-5-aminomethyl-cyclohexane and mixtures thereof.

Particularly suitable amines for the process of the invention with liquid-phase phosgenation are any primary monoamines and polyamines such as methylamine, ethylamine, butylamine, stearylamine, phenylamine, p-toluidine, 1,4-diaminobutane, 1,6-diaminohexane, 1,8-diaminooctane, 1,4-diaminobenzene, 2,4-diaminotoluene, 2,6-diaminotoluene, mixtures of the last two isomers mentioned, 2,2'-diaminodiphenylmethane, 2,4'-diaminodiphenylmethane, 4,4'-diaminodiphenylmethane, mixtures of the last three isomers mentioned, alkyl substituted diamines of the diphenylmethane series, for example 3,4'-diamino-4-methyldiphenylmethane, polyamine mixtures of the diphenylmethane series as are obtained in a known manner by aniline-formaldehyde condensations, p-xylenediamine, perhydrogenated 2,4- and/or 2,6-diaminotoluene, 2,2'-, 2,4'- and/or 4,4'-diaminodicyclohexylmethane, 1-amino-3,3,5-trimethyl-5-aminomethylcyclohexane (isophoronediamine, IPDA for short), the ethyl ester of lysine, the aminoethyl ester of lysine, 2,4- and 2,6-toluenediamine and 1,6,11-triaminoundecane.

FIGS. 1a to 1c schematically show three possible ways of carrying out the phosgenation in order to illustrate the process of the invention. FIG. 1a shows the conventional phosgenation of amines to form isocyanates, in which mixing of the starting materials and reaction of the reaction mixture are each carried out in one train (not according to the invention). FIG. 1b shows an embodiment of variant (i) according to the invention, in which the mixing zone is made up of two independently regulable trains which each comprise a mixing unit and are connected in parallel. FIG. 1c shows an embodiment of variant (iii) according to the invention, in which both the mixing zone and the reaction zone are made up of two independently regulable trains which each comprise a mixing unit and a reaction unit and are connected in parallel. "A" denotes amine, optionally mixed with solvent "(+S)", "P" denotes phosgene, optionally mixed with solvent "(+S)", "S" denotes solvent and "I" denotes isocyanate. P1>P2 means that the pressure in the first reaction unit is higher than that in the second reaction unit.

The invention will be illustrated below with the aid of examples calculated from thermodynamic and kinetic data.

COMPARATIVE EXAMPLE 1

In a plant for preparing tolylene diisocyanate (TDI) by phosgenation of TDA in the liquid phase, a 30% strength by weight solution of toluenediamine (TDA) in monochlorobenzene is mixed with a phosgene stream in a mixing nozzle (mixing time: 11.7 ms) for operation at nominal capacity. The molar ratio of phosgene to TDA is 10. The mixing temperature of the streams is about 60° C. An adiabatic tube reactor having a residence time of about 2 minutes is installed downstream of the mixing nozzle. The reaction of the amine to form isocyanate or the carbamoyl chloride as precursor occurs in this. As a result of the adiabatic temperature increase and liberation of HCl, a gas phase is formed. The two-phase reaction mixture is subsequently fed to a reaction column.

The yield in the reaction stage in respect of TDA is 93.4%.

COMPARATIVE EXAMPLE 2

The above-described plant is to produce only 50% of its nominal load. Accordingly, amine-comprising and phosgene-comprising feed streams are halved. As a result, the mixing time increases to 23.4 ms. At the same time, the residence time in the reactor doubles. The yield of TDI drops from 93.4% to 80.2%.

EXAMPLE 1

According to the Invention

The above-described plant is operated as in comparative example 2 at 50% of its nominal capacity, but the amount of the inert solvent monochlorobenzene is increased so that the concentration of toluenediamine in monochlorobenzene is 18% by weight. The total flow $G^x$, calculated as the sum of the flows of amine(s), phosgene and inert solvent, is 64% of the corresponding total flow $G^0$ in comparative example 1 for operation at nominal capacity. The mixing time is about 20.9 ms. However, the greater dilution of the TDA enables the yield to be increased back to 93.4%.

The invention claimed is:

1. A process for preparing isocyanates by reacting the corresponding amines comprised in at least one feed stream A with phosgene comprised in at least one feed stream P in a reaction plant comprising at least one mixing zone and at least one reaction zone, wherein feed stream A or feed stream P optionally comprise one or more inert materials and,
    during periods of time in which the flow $S^x$ of the amine used is below the flow $S^0$ of the amines used during operation at the nominal capacity of the reactor plant,
    (i) the ratio of phosgene to amine is increased or
    (ii) the concentration of the inert material or materials in the amine-comprising
        feed stream A or the phosgene-comprising feed stream P
            is increased compared to operation at the nominal capacity of the reactor.

2. The process according to claim 1, wherein the flow $S^x$ of the amines is below 95% of the flow $S^0$ of the amines during operation at nominal capacity of the reactor plant.

3. The process according to claim 1, wherein the flow of amine is reduced to x % compared to nominal capacity and the total flow $G^x$ of amine, phosgene and any inert materials present is at least $(x+5)\%$ of the total flow $G^0$ of amine, phosgene and any inert materials present at nominal capacity of the plant.

4. The process according to claim 1, wherein the inert material or materials is/are selected from among inert solvents and inert gases.

5. The process according to claim 1, wherein the reaction is carried out in the liquid phase.

6. The process according to claim 5, wherein the amine is present as solution or as suspension of the corresponding hydrochloride in an inert solvent in the at least one amine-comprising feed stream.

7. The process according to claim 5, wherein the amine is selected from the group consisting of methylamine, ethylamine, butylamine, stearylamine, phenylamine, p-toluidine, 1,4-diaminobutane, 1,6-diaminohexane, 1,S-diaminooctane, 1,4-diaminobenzene, 2,4- and/or 2,6-diaminotoluene, 2,2'-, 2,4'-and/or 4,4'-diaminodiphenylmethane, alkyl substituted diamines of the diphenylmethane series, for example 3,4'-diamino-4-methyldiphenylmethane, polyamine mixtures of the diphenylmethane series as are obtained in a known manner by anilineformaldehyde condensations, p-xylenediamine, perhydrogenated 2,4- and/or 2,6-diaminotoluene, 2,2'-, 2,4'- and/or 4,4'-diaminodicyclohexylmethane, 1-amino-3,3,5-trimethyl-5-aminomethylcyclohexane (isophoronediamine, IPDA for short), the ethyl ester of lysine, the aminoethyl ester of lysine, 2,4- and/or 2,6-toluenediamine, 1,6,11-triaminoundecane and mixtures thereof.

8. The process according to claim 5, wherein monochlorobenzene o-dichlorobenzene, trichlorobenzene, toluene, xylene, methylene chloride, perchloroethylene, trichlorofluoromethane, butyl acetate, hexane, heptane, octane, biphenyl, ethyl acetate, 1,2-diacetoxyethane, 2-butanone, acetonitrile, sulfane or mixtures thereof are used as solvents for the starting materials.

9. The process according to claim 5, wherein the inert material or materials added according to (ii) are selected from among the solvents used for the feed streams.

10. The process according to claim 1, wherein the reaction is carried out in the gaseous phase.

11. The process according to claim 10, wherein the inert material or materials are selected from among inert gases.

12. The process according to claim 10, wherein the product mixture obtained after the reaction is cooled in at least one quenching zone.

13. The process according to claims 10, wherein the reaction is carried out in the presence of at least one inert medium.

14. The process according to claim 10, wherein the amine is selected from the group consisting of 1,6-diaminohexane, monomeric 2,4'-methylenedi(phenylamine) and/or monomeric 2,2'-methylenedi(phenylamine) and/or monomeric 4,4'methylenedi(phenylamine), 2,4-toluenediamine and/or 2,6-toluenediamine, 1-amino-3,3,5-trimethyl-5-aminomethylcyclohexane and mixtures thereof.

* * * * *